United States Patent [19]

Lanier et al.

[11] Patent Number: 5,095,172

[45] Date of Patent: Mar. 10, 1992

[54] OLEFIN PURIFICATION PROCESS

[75] Inventors: Carroll W. Lanier, Baker; Ronny W. Lin, Baton Rouge, both of La.

[73] Assignee: Ethyl Corporation, Richmond, Va.

[21] Appl. No.: 672,486

[22] Filed: Mar. 20, 1991

[51] Int. Cl.$^5$ ............................ C07C 7/00; C07C 2/04
[52] U.S. Cl. .................................. 585/851; 585/864; 585/510; 585/521; 585/525
[58] Field of Search ............... 585/510, 521, 525, 851, 585/864

[56] References Cited

U.S. PATENT DOCUMENTS

| | | | |
|---|---|---|---|
| 2,065,540 | 12/1936 | Schneider | 260/106 |
| 3,367,987 | 2/1968 | Walsh | 260/677 |
| 3,876,720 | 4/1975 | Heilman et al. | 585/510 |
| 4,218,330 | 8/1980 | Shubkin | 252/46.6 |
| 4,300,006 | 11/1981 | Nelson | 585/10 |
| 4,527,004 | 7/1985 | Sweeney | 585/851 |
| 4,710,273 | 12/1987 | Okamoto | 203/29 |

OTHER PUBLICATIONS

Morrison and Boyd, *Organic Chemistry*, 3rd ed., Allyn and Bacon, Inc.: New York (1973), pp. 164–165.
Billmeyer, Jr., Fred, *Textbook of Polymer Science*, 2nd ed., Wiley-Interscience: New York (1972), pp. 312–315.

*Primary Examiner*—Asok Pal
*Assistant Examiner*—Nhat Phan
*Attorney, Agent, or Firm*—David M. Bunnell

[57] ABSTRACT

Vinylidene olefin is removed from an olefin mixture containing about 1 to 55 mole percent vinylidene olefin, 0 to 20 mole percent internal olefin, and the balance vinyl olefin, by:

(A) reacting the olefin mixture in the presence of a $BF_3$-water and/or organic promoter catalyst system so as to selectively dimerize said vinylidene olefin, and (B) separating said vinyl olefin and internal olefin from the dimerized vinylidene olefin to produce an olefin product having a reduced vinylidene olefin content compared to said olefin mixture.

10 Claims, No Drawings

OLEFIN PURIFICATION PROCESS

BACKGROUND

This invention relates generally to the purification of vinyl olefins and more particularly to the selective removal of branched chain olefin and especially vinylidene olefin impurities by converting them to oligomers which are easily separated from the vinyl olefins.

Olefin mixtures containing vinyl, vinylidene and internal olefins of similar carbon number are difficult to separate by distillation because they boil very close together. Such mixtures generally result when the olefins are made by a process capable of producing all three types of olefins. For example, the ethylene chain growth process using triethylaluminum followed by olefin displacement. The olefin type produced is mainly vinyl olefins, i.e. $R-CH=CH_2$, where R is an aliphatic hydrocarbon group, but the product also contains lesser amounts of internal olefins, i.e. $R-CH=CH-R$, where R is an aliphatic hydrocarbon group, and vinylidene olefins, i.e.

where R and R' are aliphatic hydrocarbon groups. When practiced to produce olefin mixtures containing up to 12 carbon atoms, the mixtures are predominantly, i.e. about 80 mole percent or more vinyl olefins. However when practiced to produce higher olefins, e.g. containing 14 or more carbon atoms, the amount of internal olefins, and especially vinylidene olefins, increases sharply such that in the $C_{16-18}$ olefin range the olefin mixture will contain about 20 to 55 mole percent vinylidene olefins and 5 to 20 mole percent internal olefins. In some uses the vinylidene olefin content of the olefin mixtures is not detrimental. However, in some uses the presence of vinylidene olefin decreases the value of the olefin mixture. For example, detergents can be made by reacting olefin mixtures with hydrogen sulfide to add hydrogen sulfide to the double bond forming a mercaptan. These in turn can be oxidized to form sulfonic acids which when converted to their salts are effective detergents. However, vinylidene olefins react with hydrogen sulfide to form tertiary mercaptans which are very difficult to oxidize to sulfonic acids. Thus, a need exists for a process for separating vinylidene olefins from a mixture containing vinyl, vinylidene and internal olefins which mixtures cannot be readily separated by distillation.

It has now been discovered that olefin mixtures containing vinyl, vinylidene and internal olefins can be upgraded to lower the vinylidene olefin content by reacting the mixture using a $BF_3$-promoter catalyst system to preferentially dimerize the vinylidene olefins. The dimerized product is not only easily separated from the product mixture by distillation, but the product, especially after hydrogenation to remove residual unsaturation, is a useful synthetic oil such that the purification process is very economical.

SUMMARY OF THE INVENTION

In accordance with this invention there is provided a process for the selective removal of vinylidene olefin from an olefin mixture containing about 1 to 55 mole percent vinylidene olefin, 0 to 20 mole percent internal olefin and the balance vinyl olefin, said process comprising:

(A) reacting said olefin mixture in the presence of a $BF_3$-water and/or organic promoter catalyst system so as to selectively dimerize said vinylidene olefin, and (B) separating said vinyl olefin and internal olefin from the dimerized vinylidene olefin to produce an olefin product having a reduced vinylidene olefin content and an increased vinyl olefin content compared to said starting olefin mixture.

DETAILED DESCRIPTION

The process is especially useful in removing vinylidene olefins from olefin mixtures made by the Ziegler Process of ethylene chain growth on triethylaluminum followed by olefin displacement. Such olefin products contain about 4 to 30 or more carbon atoms depending on reaction conditions. When used to make olefin containing 12 or less carbon atoms the products are predominantly (i.e. over 80 mole percent) linear vinyl olefins and contain lesser amounts of vinylidene and internal olefins. Such olefins are represented by the following formulas:

Vinyl Olefins 

Vinylidene Olefins 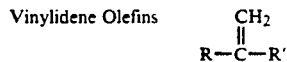

Internal Olefins 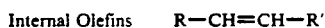

wherein R and R' are alkyl groups.

When the Ziegler Process is used to make higher olefins, the amount of internal and vinylidene olefins increases and also more chain branching occurs. In general the present process can be used to upgrade an olefin mixture wherein the olefins contain about 6 to 30 carbon atoms of which about 1 to 55 mole percent are vinylidene, about 0 to 20 mole percent are internal and the balance are vinyl olefins. More often the olefin mixtures will contain at least some internal olefins and have the composition of about 1 to 50 mole percent vinylidene, about 1 to 20 mole percent internal and the balance vinyl olefins. The olefin mixtures from the chain growth process can be separated into olefin isomers of a single carbon number such as hexenes or octenes or a mixture of carbon numbers such as $C_{12}$ to $C_{14}$ or $C_{16}$ to $C_{20}$ for use as feed materials for the process of the invention.

Suitable promoters for use in combination with $BF_3$ are water and/or organic materials such as alcohols (e.g. isopropanol, n-butanol, 1-decanol and the like), organic acids (e.g. carboxylic acids such as acetic acid, valeric acid, caproic acid or other fatty acids, sulfonic acids and the like), polyhydric alcohols (e.g. glycol, glycerol and the like), ketones (e.g. acetone, methyl ethyl ketone and the like), aldehydes (e.g. butyraldehyde and the like), acid anhydrides (e.g. acetic anhydride and the like), dialkyl ethers (e.g. diethyl ether, di-n-butyl ether and the like, dioxane, glycol ethers (e.g. ethylene glycol monomethylether (2-methoxy ethanol), ethylene glycol monoethylether, diethylene glycol diisobutylether, propylene glycol monoethylether and the like), and fatty acid alkyl esters (e.g. methyl acetate, ethyl propionate, ethyl valerate, methyl oleate and the like). The ethers, esters, anhydrides, ketones and aldehydes provide good promotion properties when combined with other promoters which have an active proton e.g. water or alcohols. Mixtures of other of the above promotors can also be used. A preferred type of organic promotors are alcohols and especially low carbon number alcohols such as n-butanol in a $BF_3/ROH$ mole ratio of about 0.7 to 1.3/1.0 and especially mole ratios of 0.80 to 1.1/1.0.

The amount of promoter can range from about 0.1 to 10 mole percent of olefin mixture.

The time and temperature are chosen to minimize the amount of isomerization and dimerization of the vinyl olefins while reducing the vinylidene olefins to the desired level. Suitable temperatures range from about $-20°$ to $80°$ C. and reaction times from about 1 to 120 minutes. The process can achieve an 80 percent or greater reduction in the amount of vinylidene olefins in the mixture with less than about a 20 percent, and preferably less than about a 5 percent, conversion of the vinyl olefin to dimer.

The process is further illustrated by, but is not intended to be limited to, the following examples.

EXAMPLE 1

To a plastic bottle were charged 2.62 grams of n-butanol and 2.73 grams of $BF_3$ were bubbled into the bottle to provide a $BF_3$/n-butanol mole ratio of about 0.99/1. The bottle was cooled and 109.3 grams of a mixture of olefins having the composition set out in Table I were added. The temperature of the reaction mixture after adding the olefins was about $35°$ C. and the reaction mixture was immediately cooled in a water-ice bath to about $5°$ to $10°$ C. Samples of the mixture were taken at 5, 10 and 30 minute intervals, quenched and analyzed by gas chromatography (G. C.) The analysis is shown in Table I in area percent.

TABLE 1

| Time | $C_{14}$ | $VC_{16}$ | $AC_{16}$ | $VC_{18}$ | $AC_{18}$ | $VC_{20}$ | $AC_{20}$ | Dimer |
|---|---|---|---|---|---|---|---|---|
| 0 (feed) | 0.88 | 7.50 | 51.97 | 8.14 | 23.47 | 2.82 | 2.97 | 0 |
| 5 | 0.71 | 0.15 | 48.47 | 0.90 | 24.21 | 2.16 | 3.65 | 18.11 |
| 10 | 0.63 | 0.23 | 43.57 | 1.76 | 21.84 | 1.38 | 3.30 | 26.41 |
| 30 | 0.54 | 0.79 | 39.49 | 1.35 | 20.73 | 0.93 | 3.53 | 31.77 | where:
VC = vinylidene olefins.
AC = alpha-olefins with a small amount, <5%, of internal olefins.

The results show that after 5 minutes the total vinylidene content had been reduced from about 18.5 percent to only about 3.2 percent, or more than an 80 percent reduction, with the production of about 18 percent dimer. After subtracting the dimer, the olefin reaction mixture contains only about 4 percent vinylidene olefins and over 90 percent vinyl olefins.

The subsequent samples at 10 and 30 minutes had about the same total amount of vinylidene content with increased dimer. This demonstrates that the vinyl olefins were dimerized only after most of the vinylidenes had been dimerized such that the initial reaction was very selective in reducing the vinylidene olefin content of the mixture. The catalyst can be deactivated, such as by quenching with water, after the initial dimerization so as to minimize vinyl consumption.

Following the dimerization step, the dimer is readily separated from the remaining olefin mixture by conventional distillation of the olefins to provide a vinyl olefin product having a greatly reduced vinylidene content compared to the original olefin mixture. The liquid dimer by-product is useful as a synthetic fluid for lubricant applications especially after hydrogenation which improves its oxidation resistance.

What is claimed is:

1. A process for the selective removal of vinylidene olefin from an olefin mixture containing about 1 to 55 mole percent vinylidene olefin, 0 to 20 mole percent internal olefin and the balance vinyl olefin, said process comprising:
   (A) selectively dimerizing said vinylidene olefins by reacting said olefin mixture in the presence of a $BF_3$-water and/or a $BF_3$-active proton containing organic promoter catalyst system, and
   (B) producing olefin product having a substantially reduced vinylidene olefin content and an increased vinyl olefin content compared to said starting olefin mixture by separating said vinyl olefin and internal olefin from the dimerized vinylidene olefin.

2. The process of claim 1 wherein said catalyst system is $BF_3$/alcohol wherein the mole ratio of $BF_3$ to alcohol is about 0.7 to 1.3/1.

3. The process of claim 2 wherein the reaction temperature is from about $-20°$ to $80°$ C.

4. The process of claim 2 wherein said catalyst system is $BF_3$/n-butanol wherein the mole ratio of $BF_3$ to alcohol is about 0.8 to 1.1/1.

5. The process of claim 1 wherein said promotor is present in an amount of from about 0.1 to 10 mole percent of olefin mixture.

6. The process of claim 2 wherein said alcohol is present in an amount of from about 0.1 to 10 mole percent of olefin mixture.

7. The process of claim 1 wherein the olefins in said olefin mixture each contain from about 6 to 30 carbon atoms.

8. The process of claim 7 wherein the olefins in said olefin mixture each contain from about 14 to 20 carbon atoms.

9. The process of claim 2 wherein said olefin mixture contains about 1 to 50 mole percent vinylidene olefin and about 1 to 20 mole percent internal olefin, the mole ratio of $BF_3$ to alcohol is about 0.8 to 1.1/1, and said alcohol is present in an amount of from about 0.1 to 10 mole percent of olefin mixture.

10. The process of claim 1 including the step of hydrogenating the dimerized vinylidene olefin after separation from said olefin product.

* * * * *

UNITED STATES PATENT AND TRADEMARK OFFICE
CERTIFICATE OF CORRECTION

PATENT NO. : 5,095,172

DATED : March 10, 1992

INVENTOR(S) : CARROLL W. LANIER and RONNY W. LIN

It is certified that error appears in the above-identified patent and that said Letters Patent is hereby corrected as shown below:

In the Claims:

Claim 1 (A), Column 4, lines 22-23 read:

"$BF_3$-water and/or a $BF_3$-active proton containing organic promoter catalyst system, and", but should read:

-- $BF_3$/alcohol and/or a $BF_3$/organic acid catalyst system, and -- .

Claim 1 (B), Column 4, line 24 reads:

"producing olefin product...", but should read:

-- producing an olefin product... -- .

UNITED STATES PATENT AND TRADEMARK OFFICE
CERTIFICATE OF CORRECTION

PATENT NO. : 5,095,172
DATED : March 10, 1992
INVENTOR(S) : Carroll W. Lanier and Ronny W. Lin It is certified that error appears in the above-indentified patent and that said Letters Patent is hereby corrected as shown below:

Claim 5, Column 4, line 37 reads:

"...wherein said promotor is", but should read:

-- ...wherein said alcohol or organic acid is -- .

Signed and Sealed this

Third Day of August, 1993

Attest:

MICHAEL K. KIRK

*Attesting Officer*  *Acting Commissioner of Patents and Trademarks*